United States Patent [19]

Davis et al.

[11] Patent Number: 5,487,298

[45] Date of Patent: Jan. 30, 1996

[54] INERTIAL HOPKINSON BAR SHOCK SENSOR

[75] Inventors: William R. Davis, Darlington; Willard S. Walton, Churchville, both of Md.

[73] Assignee: The United States of America as represented by the Secretary of the Army, Washington, D.C.

[21] Appl. No.: 215,878

[22] Filed: Mar. 22, 1994

[51] Int. Cl.$^6$ .................................................. G02M 7/00
[52] U.S. Cl. .......................... 73/12.05; 73/12.08; 73/167
[58] Field of Search ............................. 73/12.04, 12.05, 73/167, 12.06, 767, 774, 775

[56] References Cited

U.S. PATENT DOCUMENTS

| | | | |
|---|---|---|---|
| 3,525,250 | 8/1970 | Hurst | 73/12.08 |
| 3,872,709 | 3/1975 | Pagano | 73/12.01 |
| 4,126,039 | 11/1978 | Smith et al. | 73/167 |
| 4,376,388 | 3/1983 | Soper | 73/167 X |
| 4,379,401 | 4/1983 | San Higuel | 73/12.08 |
| 4,423,640 | 1/1984 | Jetter | 73/862.634 |
| 4,495,792 | 1/1985 | Bai et al. | 73/12.06 |
| 4,817,435 | 4/1989 | Faller | 73/167 X |
| 5,303,596 | 4/1994 | Rickman | 73/431 X |

OTHER PUBLICATIONS

Accelerometer Calibration w/the Hopkinson Pressure Bar, (Brown, Wayne), 1963.
W. Scott Walton, "New Ballistic Shock Protection Requirement for Armored Combat Vehicles", Nov. 1989, pp. 298–309.
Jon S. Wilson, "Pyro in, garbage out", Test, Jun./Jul. 1989, pp. 12–14.
Frommer et al., "Mechanical Shock Sensors (A Feasibility Study)", pp. 239–249.
W. Scott Walton, "Blast and Ground Shock", pp. 135–149.

*Primary Examiner*—Richard Chilcot
*Assistant Examiner*—Elizabeth L. Dougherty
*Attorney, Agent, or Firm*—Freda L. Krosnick; Charles H. Harris

[57] ABSTRACT

A device and method for measuring the intensity of high amplitude strain waves caused by the impact of a projectile or the detonation of an explosive on armor plate are disclosed. The sensor may be configured as a shock wave sensor. The shock wave sensor may include a solid, cylindrical bar having a pair of strain gages located at opposite positions on an exterior surface of the bar. The strain gages may be located along one end of the bar proximal to a test specimen such as armor plate.

15 Claims, 4 Drawing Sheets

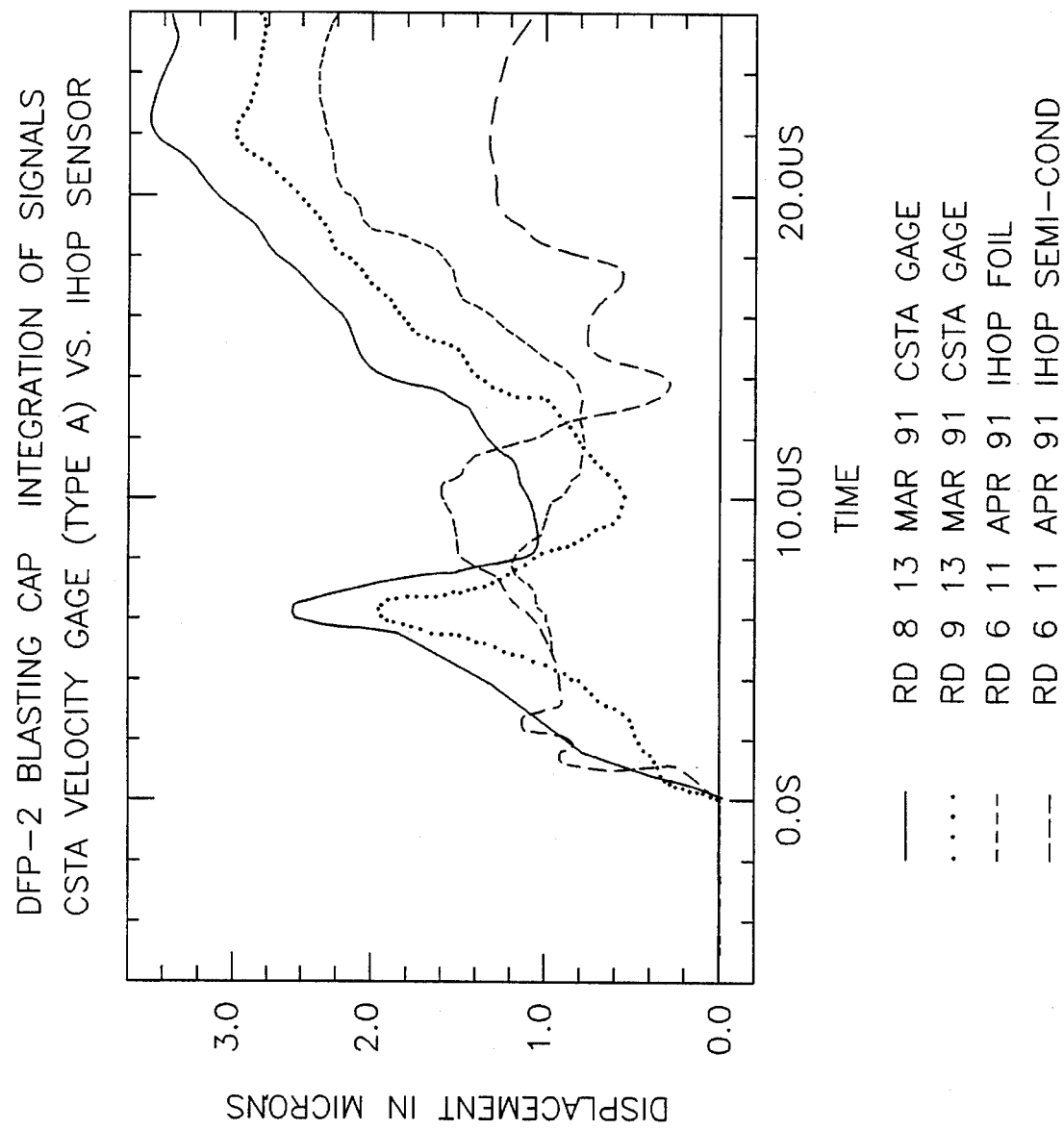

5,487,298

INERTIAL HOPKINSON BAR SHOCK SENSOR

BACKGROUND OF THE INVENTION

1. Field of the Invention

The invention relates generally to force-motion measurement devices, and specifically to devices for measuring the force-motion and energy of waves moving through solid (metallic) objects.

The Combat System Test Activity (hereinafter referred to as CSTA) velocity gage of the prior art uses the principle of electromagnetic induction to generate a signal. The signal amplitude is proportional to the speed of the movement of a coil of fine wire with respect to a relatively stationary magnet.

The instant invention, the Inertial Hopkinson Bar Sensor (hereinafter referred to as IHOP) gage, instead measures the actual expansion and contraction of the metal surface of the rod using a strain gage. The IHOP gage is passive because only the resistance of the strain gage changes as it stretches. An electrical current supplies the excitation. The IHOP gage gives a direct measurement of the contraction of the rod and thus of the amplitude of the deformation wave moving through the plate.

The chief advantage in the IHOP gage is its resistance to breakdown or detachment, when subjected to very large amplitude high frequency shock, such as that experienced in close proximity to the impact point of a large high speed projectile.

2. Description of the Prior Art

Devices of various types have been used for many years in attempts to measure the energy of projectiles and their effect upon armor plate. The present state of the art includes strain gages of various types as well as several types of velocity gages which use electromagnetic effects to measure the velocity of a surface. A summary of the present state-of-the-art is presented in a paper by Mr. Willard Scott Walton entitled "New Ballistic Shock Protection Requirement for Armored Combat Vehicles" contained in the 60th Shock and Vibration Symposium Vol. I (David Taylor Research Center, Bethesda, Md.).

Mr. Hopkinson reported the use of an instrumented bar to measure shock in 1919. His work has been built upon by many investigators since that time. Notable among them is Mr. R. Sill who reported upon the use of the Hopkinson bar to calibrate sensors. The Hopkinson bar concept is presently being used in many laboratories to calibrate sensors and to experiment with shock waves.

References teaching shock measurement including those measuring shock of impact upon armor plates or solid bodies are well known in the art. Exemplary of those include U.S. Pat. No. 4,379,401, issued to Anthony San Miguel which teaches a system designed to measure only the amplitude of maximum plate movement (deformation).

The plate is pushed backward at high speed by some force and the apparatus as described is akin to a series of off-on switches at different distances from the plate. The plate hits each switch sequentially as it moves backward and the last switch to be contacted gives a rough approximation of the total motion of the plate.

U.S. Pat. No. 3,872,709 issued to Victor H. Pagano, discloses a method for measuring the resistance of a plate which is being fractured by some dynamic force. The method provides no data for the shock or vibration of tile plate, no time-amplitude history of the deformation. The method can be used only once per sample. The data provided is discrete. That is, it is test dependent upon the discrete number of grooves machined in the plate. The method is useful for evaluating plate quality only if the exact energy input is known.

U.S. Pat. No. 3,525,250 issued to William M. Hurst teaches mechanical gages for measuring the approximate amplitude of shock waves in air. A thin sheet of metal is pushed into grooves of various depths. A higher pressure is required to deform the sheet metal into the deeper grooves. First, the deformable gage is incapable of measuring shock levels in armor plate, only in air. Again no signals are produced which record the amplitude-time history of a shock wave. The gages are incapable of being used to measure shock in armor plate.

Jon S. Wilson, "Pyro-In, Garbage Out", *Test Engineering & Management*, pp. 12–14, June/July 1989 discusses accelerometer mounts and the CSTA velocity gage.

David Frommer, et al, *"Mechanical Shock Sensors (A Feasibility Study)"*, 59th Shock and Vibration Symposium, Sandia Report SAND88-2473, Volume III, pp. 239–249, 1988. This reference discusses the mechanical sensor concept.

While directed to measuring shock waves in armor plates, the study was directed to various sensors such as piezo and IR film sensors, magnetic sensors and copper-ball sensors. W. Scott Walton, "Dynamic Response of Armor Plate to Non-penetrating Projectile Impact", *Shock and Vibration Bulletin No. 56* pp. 135–149 1986, refers to the CSTA velocity gage. The IHOP and CSTA velocity gage have the same objective but differ in techniques as will be described, hereinbelow.

BRIEF DESCRIPTION OF THE INVENTION

There is provided in accordance with this invention a device used to measure the intensity of high amplitude strain waves caused by the impact of a projectile or the detonation of an explosive on armored vehicles.

The device of the invention uses a round bar similar to a Hopkinson bar. The bar used in the device is smaller in size than the Hopkinson bar and welded to a shock target in order to efficiently transmit the shock waves into the bar. The bar is of a very small size in order to maximize high frequency response and of a sufficient length to allow all of the shock event to flow past the sensors (strain gages) before any reflected waves return to interfere with the recording.

The invention answers the need for a device to measure impact dynamics under severe conditions such as the back side of an armor plate directly behind the impact point of a projectile (or the detonation point of high explosive). All shock sensors having such velocity gages and strain gages are unable to survive in the immediate vicinity of an impact. They either break or detach from the plate.

Other methods of indirect measurement are impractical to use in a field environment either because of the massive support they require or an unlimited access to the plate which is not available.

BRIEF DESCRIPTION OF THE DRAWINGS

FIG. 4 is a plot comparing the integrated signal of the IHOP sensor to the integrated signal from a CSTA velocity gage.

DETAILED DESCRIPTION OF THE PREFERRED EMBODIMENTS

Figure 1:
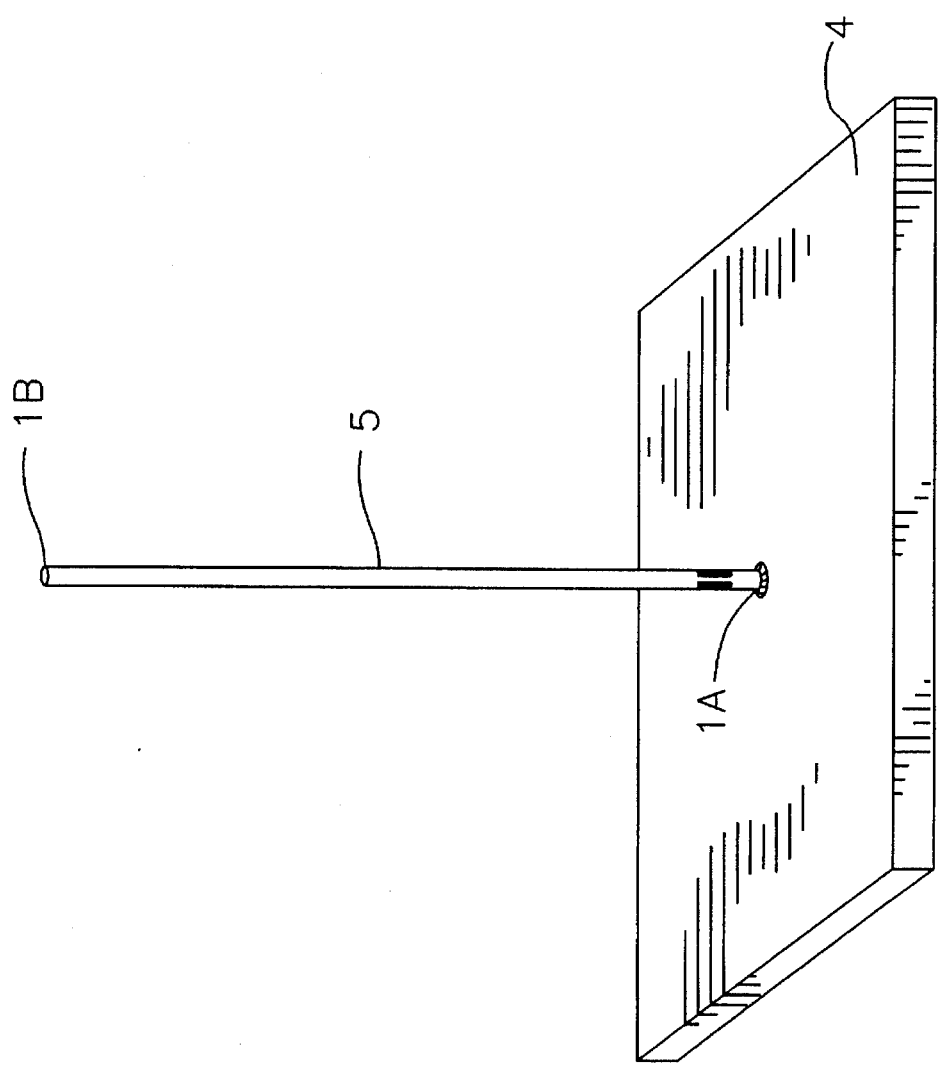
FIG. 1 is a side view of the device as it is attached to a piece of armor plate for measurement of the shock induced by the impact of a projectile.

The Inertial Hopkinson Bar (IHOP) sensor device generally identified as 5 in FIG. 1 is a round bar or rod 1 welded at one end 1a, to the object under test such as a armor plate 4.

Figure 2:
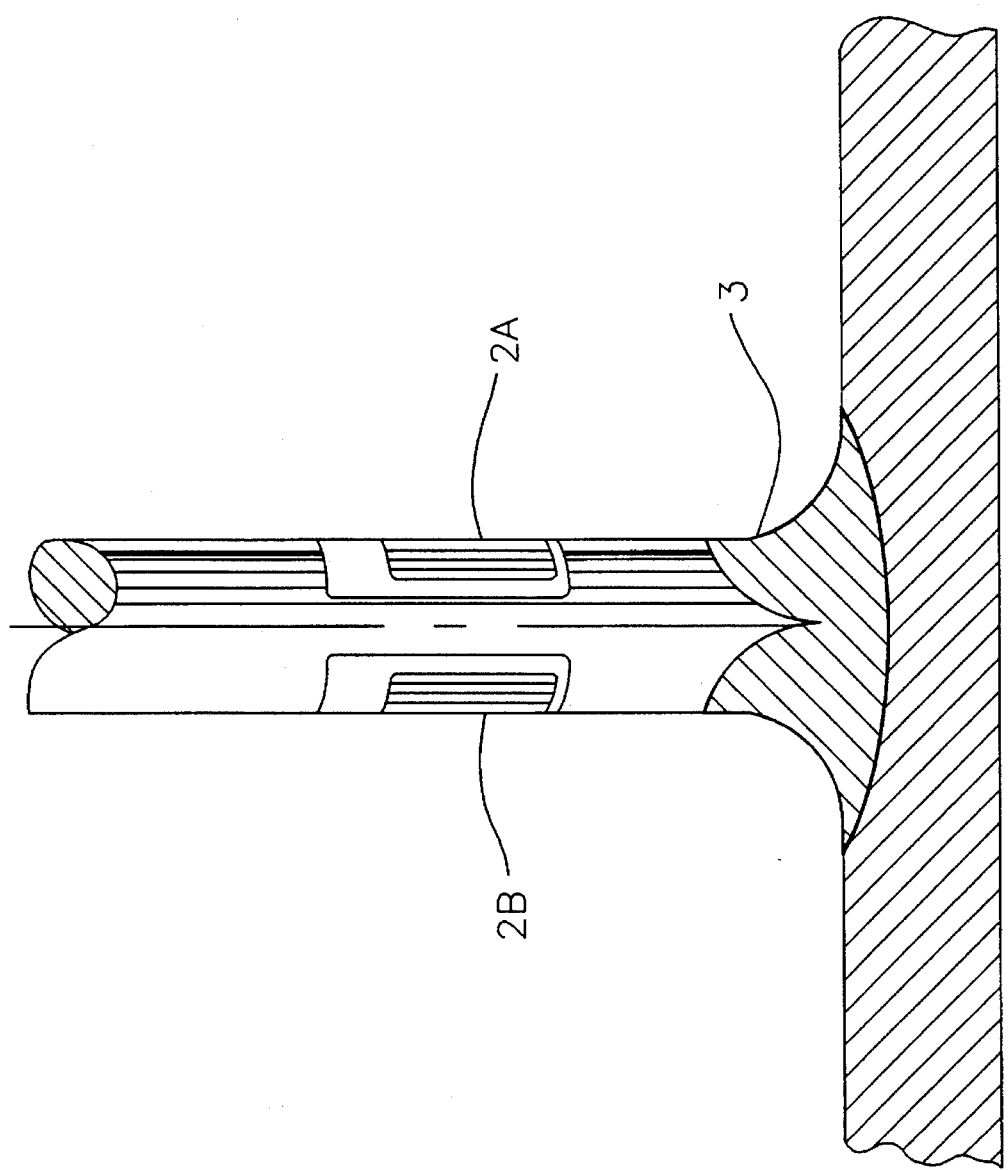
FIG. 2 is a cut-away view of the strain gages positioned on the IHOP bar.
Figure 3:
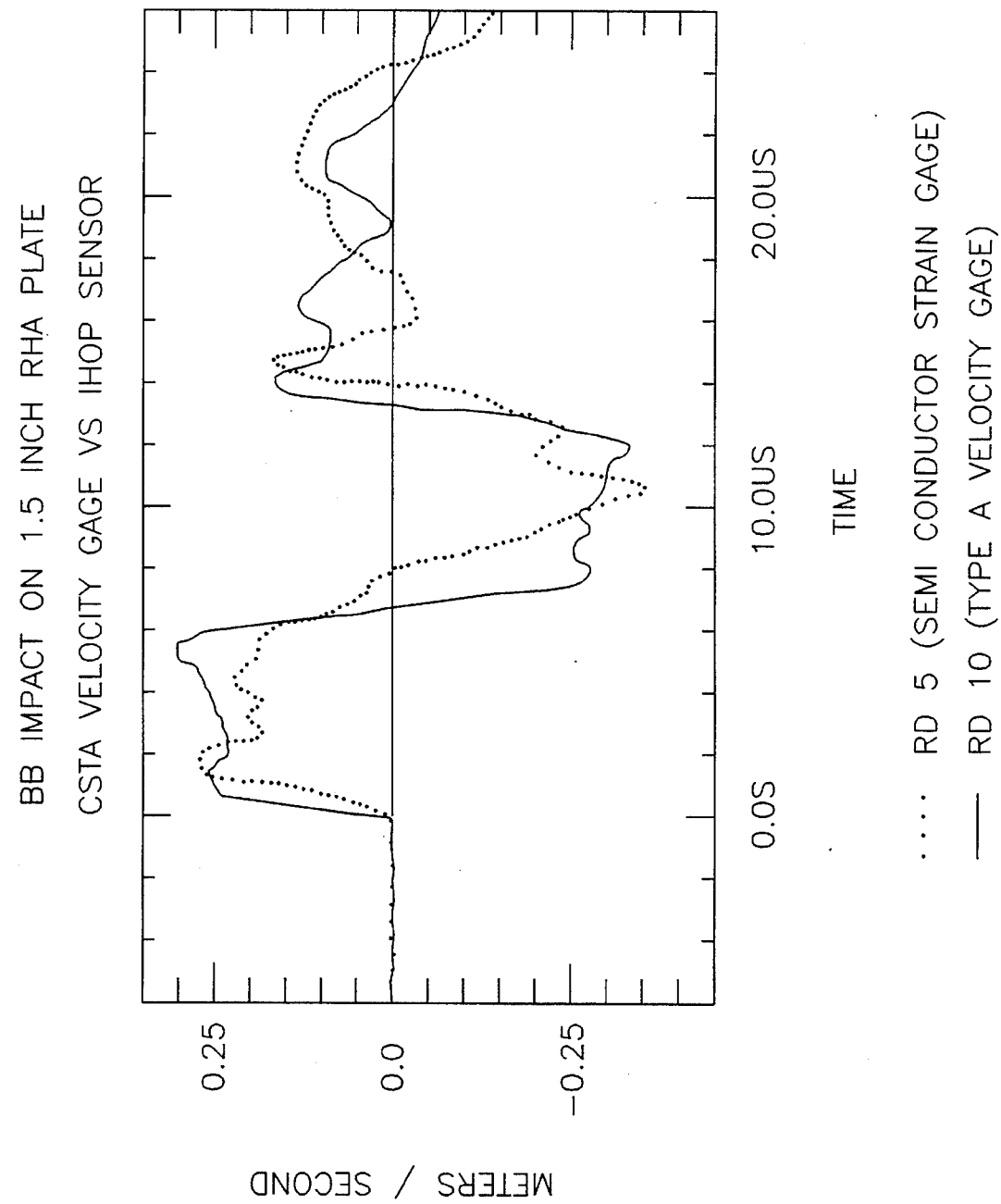
FIG. 3 is a plot of measurements from a BB impact on a 1.5" thick plate of Rolled Homogeneous Armor (RHA) as shown.

The two strain gages 2a and 2b as seen in FIGS. 1 and 2, are located near the end of the bar 1 and adjacent to the object 4. Bar 1 is of a small diameter, preferably, $5/32$ inch diameter or less for optimum frequency response, and is welded at end 1a to the object 4 under test with a through penetration weld 3, having smooth contours.

Bar 1, having ends 1a and 1b, is at least eighteen inches in length and constructed of a metal, preferably steel so as to ensure that the shock event fully passes the affixed strain gages 2a and 2b before strain energy is reflected from end 1b of the bar 1 and returns to interfere with the recording the event.

Development of IHOP gage sensor 5 demonstrated during tests that the diameter of the bar is critical in obtaining the optimal frequency response and that the length of the bar is also critical, in that is must be long enough to allow all of the shock event to pass gages 2a and 2b before reflections return to interfere with the recording. Strain gages 2a and 2b are affixed to bar 1 on diametrically opposite sides as best seen in FIG. 2, and connected so as to record longitudinal strain without any bending strain. The IHOP gage 5, using a $5/32$ inch diameter bar 1 measures the amplitude of shock waves with frequencies below 500 KHz with event durations less than 73 microseconds. The IHOP gage 5 is easily attached, uses common material, and has very good high frequency response for recording severe shock events. The test model of this invention has survived repeated dynamic events without resulting in damage as has been characterized as problematic in prior art gage type sensors.

As seen in FIGS. 1 and 2, strain gages 2a and 2b are positioned directly opposite each other near the end of bar 1 and adjacent to the object under test. The gages 2a and 2b are connected in a measurement circuit (Wheatstone bridge circuit) in such a way as to negate the effect of any bending of the bar during the test. Only longitudinal strain is measured. Strain gages with high frequency response and the ability to withstand high dynamic strains are required.

The instrumentation required to record the strain gage output is typically a recording oscilloscope configured with suitable cabling and preamplifier to give superior high frequency response.

In operation, the IHOP bar sensor 5 is affixed by a penetration weld 3 to the back side of armor plate 4. The back side of armor plate 4 is best defined as the side behind which impact takes place. Upon impact, the IHOP sensor 5 measures longitudinal strain in the device through strain gages 2a and 2b. The position of strain gages 2a and 2b on bar 1 negate the effect of any vibratory motion experienced by bar 1 and measures the longitudinal strain experienced by bar 1.

RESULTS OF TESTING

Successful tests of the Inertial Hopkinson Bar Shock Sensor (IHOP) were conducted on 11 Apr. 1991. Plots from two different types of measurements from a BB impact on a IHOP sensor has slower rise time (2 microseconds) than the CSTA velocity gage, but otherwise the two measurements generally agree both in shape and magnitude.

FIG. 4 shows a comparison of the integrated signal of the IHOP sensor to the integrated signal from a CSTA velocity gage.

The measurements were obtained during the detonation of a DFP-2 blasting cap. The blasting cap excited a high frequency resonance (3 MHz) in the IHOP sensor. Some differences in waveform shape become apparent at 6 microseconds, but in general, the waveforms are of approximately the same magnitude and shape.

What is claimed is:

1. A sensor for use with a test specimen comprising:

a bar;

a first strain gage attached to said bar; and a second strain gage attached to said bar; wherein said bar is attached onto a back surface of the test specimen, said bar positioned on the back surface of the test specimen so as to be located directly behind an impact-receiving front surface of the test specimen.

2. A sensor as defined in claim 1, wherein said bar is located between said first and second strain gages.

3. A sensor means as defined in claim 2, wherein said bar is a cylindrical bar having a diameter less than or equal to $5/32$ inches.

4. A sensor as defined in claim 3, wherein said bar is at least 18 inches in length.

5. A sensor of claim 2, wherein said bar comprises at least a metal.

6. A sensor of claim 5, wherein said metal is steel.

7. The sensor according to claim 1, wherein said bar has an end proximal to the test specimen, and said strain gages are located at said end of said bar proximal to the test specimen.

8. A sensor for measuring the intensity of high amplitude energy waves having amplitude frequencies below 500 KHZ with event durations less than 73 microseconds, the waves resulting from impact of a projectile or detonation of an explosive on a test specimen, said sensor comprising:

a bar;

a first strain gage located on said bar; and a second strain gage located on said bar; said bar having first and second end portions, said bar positioned directly behind an impact point on a front surface of the test specimen;

said first and second strain gages positioned at an end of said bar proximal to the test specimen, said first strain gage located opposite from said second strain gage.

9. A sensor as defined in claim 8, wherein said bar comprises a diameter less than or equal to 5/32 inches.

10. A sensor as defined in claim 9, wherein said bar is at least 18 inches in length.

11. A sensor means of claim 10 wherein the bar comprises a metal.

12. A sensor means of claim 11, wherein said metal is steel.

13. The sensor according to claim 8, wherein said bar is attached to the test specimen.

14. A method for measuring the intensity of high amplitude strain waves upon impact of a projectile or detonation of an explosive on a test specimen comprising:

(1) welding a first end portion of a bar to said test specimen;

(2) attaching first and second strain gages onto said bar at a first and a second position, respectively;

(3) orienting said first and second strain gages onto said first and second positions so that said gages are positioned opposite to each other;

(4) connecting said first and second strain gages in a measurement circuit so as to negate any bending effect on said bar;

(5) impacting a surface of the test specimen with shock waves;

(6) measuring longitudinal strain only.

15. The method for measuring the intensity of high amplitude strain waves upon impact of a projectile or detonation of an explosive on a test specimen according to claim 14, wherein the step of welding a first end portion of a bar to said test specimen further comprises welding the first end portion of the bar to the test specimen so the bar and the test specimen define a perpendicular orientation.

\* \* \* \* \*